United States Patent [19]

Westphal

[11] 4,392,645
[45] Jul. 12, 1983

[54] HEAD SUPPORT AND HALO JIG

[76] Inventor: Thomas R. Westphal, 143B E. Frederick St., Lancaster, Pa. 17602

[21] Appl. No.: 268,007

[22] Filed: May 28, 1981

[51] Int. Cl.³ .............................................. A61G 13/00
[52] U.S. Cl. ..................................... 269/328; 269/45; 269/77
[58] Field of Search ...................... 269/328, 45, 77, 78, 269/71; 5/434; 128/133, 134, 76 R, 84 R, 87 R; 414/736, 591

[56] References Cited

U.S. PATENT DOCUMENTS

| 456,891 | 7/1891 | Fish | 269/45 |
| 1,054,246 | 2/1913 | Stauffer | 269/78 X |
| 2,669,958 | 2/1954 | Sweeney | 269/45 |
| 3,810,462 | 5/1974 | Szpur | 269/328 X |
| 4,253,649 | 3/1981 | Hewson | 269/45 |

OTHER PUBLICATIONS

Prior Art Device in use at Hershey Medical Center, Department of Orthopedics, Hershey, Pa. Displayed at American Spinal Injury Assoc. Meeting Mar. 26, 1981, New Orleans, La.
Head Positioning Device for Applying Halo Traction by Michael S. Weiss, M.D., Conal B. Wilmot, M.D. p. 89, Arch. Phys. Med. Rehabil. vol. 62, Feb. 1981.

Primary Examiner—James G. Smith
Assistant Examiner—Steven P. Schad
Attorney, Agent, or Firm—Martin Fruitman

[57] ABSTRACT

A temporary support structure for the head of a surgical patient combined with an alignment fixture for a steel band to be attached to the patient's head for subsequent attachment to a head and neck support system. A self-standing adjustable pillar is used to support a patient's head as it protrudes over the edge of a bed or table. A three-lobed head support atop the pillar furnishes support to the head while restricting head movement. Also attached to the pillar, by use of several adjustable clamps, is a jig to hold a metal halo for attachment to the patient's skull.

2 Claims, 1 Drawing Figure

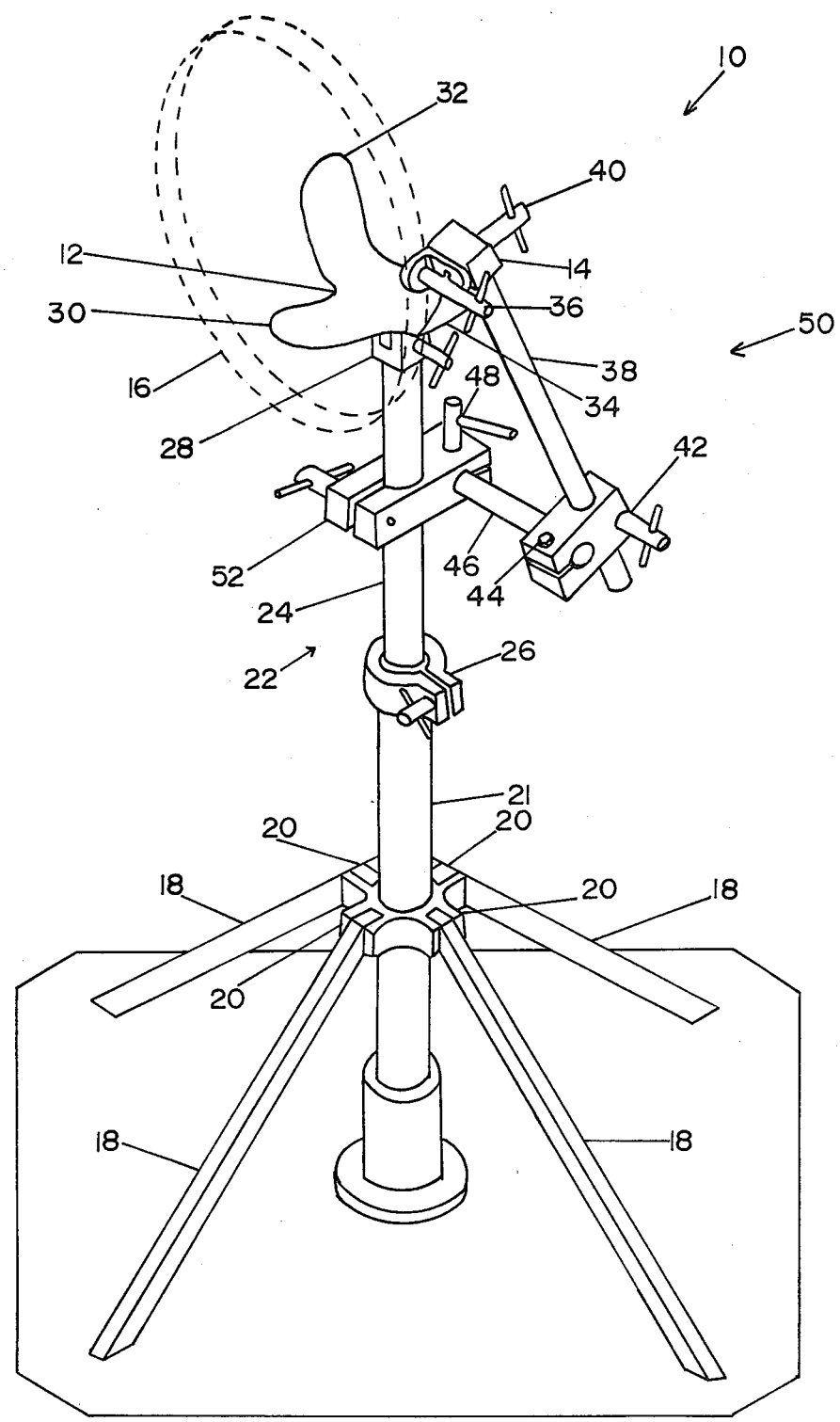

HEAD SUPPORT AND HALO JIG

SUMMARY OF THE INVENTION

This invention pertains generally to surgery and more specifically to a head restraint for use in temporarily immobilizing a patient's head and neck while a more permanent device is implemented.

An important aspect of treatment when a person suffers a "broken neck"—a fracture in the upper spine—is the immobilizing of the head for a long period in order to permit surgical repair and healing of the fracture.

The long term head restraint device normally used in modern facilities is termed a "halo". This device is a metal head band, typically stainless steel, which is actually mechanically attached to the patient's skull by pressure bolts which contact the skull at several specific points. The halo is then attached to several support rods which are themselves supported from a harness on the patient's body. The patient's head is thereby rigidly oriented and immobilized for a long term recuperative period, but since the head support structure is attached to the body and is relatively light weight, the patient is not totally immobilized and can be transported about.

Despite the sophisticated nature of the long term head support, the process of its initial installation has remained largely a brute force effort.

Until recently the standard procedure for the attachment of the halo ring was by using manual support, that is, the hands of an assistant, sometimes with a crude plank under the patient's shoulders and upon which the head rested. Such an assistant would stand at the end of a surgical table, with the patient's head extending over the end of the table, and hold the patient's head with his hands. Aside from the fact that such a method tied up an assistant who would be more valuable elsewhere, the system had some other severe drawbacks.

For instance, the assistant's position blocked access to the patient's head from exactly the direction which the halo must be slipped onto the patient's head. The assistant's arms, generally extended so that his hands could the head, essentially had to be temporarily moved, one at a time, to permit the halo to be placed on the head. This manipulation makes the entire process difficult and dangerous to the patient.

But even more important, the patient's wellbeing depends strongly on the ability of such manual support to hold a single position of the patient's head for long periods. This requirement is further complicated because the patient may be hostile and be attempting to move, displace the halo or break loose from the assistant's support.

Some less crude methods not do exist. For instance, there are simple head supports made for attachment to specific tables or frames by clamping means. While such devices present some benefit above the prior manual support methods, they do not solve the problem of proper accurate alignment of the halo with the patient's head.

The present invention solves not only the problems of accessibility and stability of support but also the problem of accurate halo alignment by the use of a freestanding support system which uses only a single point of support for the patient's head, with that point being well below the point of attachment of the halo. The area of the head to which the halo must be attached is, therefore, left free. Moreover, since no one is standing beyond the head of the patient, that region is easily accessible for placing the halo on the head, or for any other task associated with the procedure.

The support structure of the invention involves a multi-legged floor support, with the legs either rigid or folding, and a vertical pillar supported by the support and extending approximately from the floor level to the region directly under the rear of the base of the patient's head. On the top of the pillar is located a three-lobed head support, two lobes extending toward the patient's ears and the third lobe extending along the rear of the skull a short distance toward the top of the head. The three lobes are curved upward from their junction, which is essentially in the horizontal plane, in order to form a cradle for the head. The curvature of the lobes is sufficient so that, because of the weight of the head, head movement is completely restrained once the head is placed within the cradle, while the neck and head are extended beyond the end of the table for easy accessibility.

In order to effect the versatility required to use the head support on any patient and with any body support, several adjustable clamps are used in the head support system. Thus, the pillar height is adjustable by means of a clamp and telescope arrangement, and the rake of the head cradle is adjustable by means of a clamp and pivot arrangement at the top of the pivot. Rotation of the cradle in the horizontal plane can be accomplished either by rotation of the telescopic elements at their clamping point or by rotation of the entire assembly.

Head support is, however, not the only function of the invention. Whereas the manual support method cannot serve in any way as a locating system for the halo, the present invention acts both as support and as an accurate and stable means to locate the halo. Furthermore, the halo locating function is directly related to the position of the patient's head as it is held in the cradle, so that movement of the rest of the patient's body or the supporting table or lack of coordination between the several people working on the patient, has no effect on the halo's location. Provided only that the patient's head does not move within the cradle, the halo's location on the head is completely determined by adjustment of the several clamps which hold the halo onto the head supporting pillar.

A split ring clamp is used to attach the halo locating system onto the head support pillar at a point between the telescope clamp and the cradle swivel clamp. This split clamp permits the position of the halo to be vertically adjusted. Two extension rods, each attached by clamped swivel joints, one extending outward and the other upward from the pillar location below the patient's head, permit the halo holder clamp to be located in virtually any orientation relative to the patient's head. Once oriented, however, when all the clamps are tightened, no change of orientation will occur between the patient's head and the halo.

Accurate installation of the halo with minimum effort is therefore assured, with no danger of movement of the patient's head because of wavering support from or relocation of an assistant's hands.

BRIEF DESCRIPTION OF THE DRAWING

The FIGURE is a perspective view of the preferred embodiment of the invention.

STRUCTURE OF THE PREFERRED EMBODIMENT

The preferred embodiment of the invention is shown in the FIGURE where the head support and halo jig assembly 10 is shown in a perspective view with head support 12 and halo holder 14 shown ready to accept a patient's head and a halo 16 (shown in phantom view).

Assembly 10 is constructed to rest on the floor directly under a patient's neck and head as the patient's body is largely supported on a bed or surgical table, but with the patient's head and shoulders extending over the end of the support. Assembly 10 thus acts as a support for the head, but since it is located directly below and out of the way, it does not interfere in any way with access to the patient.

Several legs 18 are used to support assembly 10, and for ease of transportation and storage, legs 18 are pivoted at connections 20 so that they can be folded flat against the lower portion 21 of pillar 22. Pillar 22 and telescoping section 24 are the essential support system for head support 12 and halo holder 14. The vertical location of head support 12 and halo 16 are adjustable to an approximate location for each patient and support table by means of telescope clamp 26. Loosening clamp 26 permits the lengthening or shortening of the combined length of lower section 21 and telescoping section 24.

Head support 12 is attached to the top of pillar 22 by means of pivot clamp 28 which permits the tilting of head support 12 relative to the horizontal plane for exact orientation relative to the patient's head. Head support 12 is itself constructed of three lobes 30, 32 and 34. When the patient's head is at rest within head support 12, lobes 32 and 34, curved to essentially conform to the head, are pointing toward the patient's ears, while lobe 30 which is curved upward only slightly is oriented pointing toward the top of the patient's head. Together, lobes 30, 32, and 34 form a cradle for the head and completely restrict head movement, including turning and lifting, while the complete adjustability of the orientation of head support 12 permits the surgeon to position the head in an optimum position without additional traction.

Halo 16 is held in a stable orientation relative to the head by attachment to halo holder 14 with turnscrew 36. Halo holder 14 is itself adjustably attached to rod 38 by clamp 40. Rod 38 is oriented essentially vertically but is independently adjustable in the horizontal plane by use of clamp 42 and in the vertical plane by clamp 44. Clamp 44 connects rod 38 to rod 46 which is itself also rotatable by means of clamp 48. The entire halo support system 50 is attached to pillar 22 by means of clamp 52 located between head support pivot clamp 28 and telescope clamp 26. The basic height adjustment of halo 16 relative to head support 12 is available by sliding clamp 52 on telescoping section 24.

OPERATION OF THE PREFERRED EMBODIMENT

When in actual use the sequence of adjustment of the invention is as follows:

Assembly 10 is located at the end of any available table or stretcher and legs 18 are spread out for stability. Telescope clamp 26 is then loosened, telescoping section 24 raised to a height appropriate for the patient and clamp 26 tightened.

Pivot clamp 28 is then loosened and head support 12 oriented to accurately restrain the patient's head in the proper position. Clamp 28 is then tightened.

Halo 16 is placed around the patient's head and adjusted by attaching it to halo holder 14 by use of clamp 36 and then adjusting various clamps 40, 42, 48, and 52 for the halo's exact location.

Once halo 16 is accurately located the clamps are all tightened and the halo is ready for installation on the head with absolute assurance that the orientation will not vary.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

For example several clamps in the present embodiment are redundant. Clamp 48 and clamp 44, for instance, perform the same function, and one can be eliminated. Moreover, other adjustment means could be used for orienting the functioning assemblies and the legs need not necessarily be foldable.

What is claimed as new and desired to be secured by Letters Patent of the United States is:

1. A head support and halo locating jig for use in attaching a halo band to the head of a patient positioned with neck and head extending off the end of a patient support means, comprising:
    a base means resting on the floor below the patient's neck and head;
    a pillar means movably attached and clamped to the base means and extending vertically upward to the region just below the patient's head;
    a head support cradle pivotably attached to permit movement in only a single vertical plane and clamped to the top of the pillar means; and
    a halo locating system adjustably clamped to the pillar independent of the head support cradle attachment means, including at least two clamped swivel adjustments independent of the head support cradle adjustment, and holding the halo band in a stable, predetermined position relative to the head support means.

2. A head support and halo locating jig for use in attaching a halo band to the head of a patient positioned with neck and head extending off the end of a patient support means, comprising:
    a base means resting on the floor below the patient's neck and head;
    a pillar means movably attached and clamped to the base means and extending vertically upward to the region just below the patient's head;
    a head support cradle, pivotably attached and clamped to the top of the pillar means, comprising three curved lobes essentially conforming to the head, two lobes curving upward to a horizontally reclining patient's ears and the third lobe curving toward the top of the patient's head; and
    a halo locating system adjustably clamped to the pillar means, including at least two clamped swivel adjustments, and holding the halo band in a stable, predetermined position relative to the head support means.

* * * * *